(12) United States Patent
Tan et al.

(10) Patent No.: US 9,953,397 B2
(45) Date of Patent: Apr. 24, 2018

(54) SYSTEM AND METHOD FOR MEDICAL IMAGE CORRECTION

(71) Applicant: General Electric Company, Schenectady, NY (US)

(72) Inventors: Ek Tsoon Tan, Mechanicville, NY (US); Xiaofeng Liu, Niskayuna, NY (US); Dan Xu, Waukesha, WI (US)

(73) Assignee: GENERAL ELECTRIC COMPANY, Schenectady, NY (US)

(*) Notice: Subject to any disclaimer, the term of this patent is extended or adjusted under 35 U.S.C. 154(b) by 143 days.

(21) Appl. No.: 14/478,597

(22) Filed: Sep. 5, 2014

(65) Prior Publication Data

US 2016/0071269 A1 Mar. 10, 2016

(51) Int. Cl.
| | |
|---|---|
| *G06K 9/00* | (2006.01) |
| *A61B 5/0436* | (2006.01) |
| *G06T 3/00* | (2006.01) |
| *A61B 5/055* | (2006.01) |
| *G06T 5/00* | (2006.01) |
| *G06T 7/32* | (2017.01) |

(52) U.S. Cl.
CPC ............... *G06T 3/00* (2013.01); *A61B 5/055* (2013.01); *G06T 5/006* (2013.01); *G06T 7/32* (2017.01); *G06T 2207/10088* (2013.01)

(58) Field of Classification Search
None
See application file for complete search history.

(56) References Cited

U.S. PATENT DOCUMENTS

| | | |
|---|---|---|
| 6,275,038 B1 | 8/2001 | Harvey |
| 6,288,540 B1 | 9/2001 | Chen et al. |
| 6,320,380 B1 * | 11/2001 | Wu .................... G01R 33/5615 324/307 |

(Continued)

FOREIGN PATENT DOCUMENTS

EP          1659943 B1    11/2012

OTHER PUBLICATIONS

Studholme et al. "Incorporating an Image Distortion Model in Non-rigid Alignment of EPI with Conventional MRI", Information Processing in Medical Imaging. IPMI 1999. Lecture Notes in Computer Science, vol. 1613, Jun. 25, 1999, pp. 454-459.*

(Continued)

*Primary Examiner* — Matthew Bella
*Assistant Examiner* — Jose M Torres
(74) *Attorney, Agent, or Firm* — Pabitra K. Chakrabarti

(57) ABSTRACT

A method implemented using at least one processor includes receiving a target image and a reference image. The target image is a distorted magnetic resonance image and the reference image is an undistorted magnetic resonance image. The method further includes selecting an image registration method for registering the target image to the reference image, wherein the image registration method uses an image transformation. The method further includes performing image registration of the target image with the reference image, wherein the image registration provides a plurality of optimized parameters of the image transformation. The method also includes generating a corrected image based on the target image and the plurality of optimized parameters of the image transformation.

21 Claims, 6 Drawing Sheets

(56) References Cited

U.S. PATENT DOCUMENTS

| | | | |
|---|---|---|---|
| 6,445,182 B1* | 9/2002 | Dean | G01T 33/4822 |
| | | | 324/307 |
| 6,700,373 B2 | 3/2004 | Mueller et al. | |
| 8,040,133 B2 | 10/2011 | Pfeuffer et al. | |
| 8,160,319 B2 | 4/2012 | Holland et al. | |
| 8,401,616 B2 | 3/2013 | Verard et al. | |
| 9,679,373 B2* | 6/2017 | Vilsmeier | G06T 7/0012 |
| 9,857,443 B2* | 1/2018 | Tadic | G01R 33/387 |
| 2003/0228042 A1* | 12/2003 | Sinha | G06T 7/0012 |
| | | | 382/131 |
| 2007/0252597 A1* | 11/2007 | Posse | G01R 33/485 |
| | | | 324/312 |
| 2008/0050043 A1* | 2/2008 | Hermosillo Valadez | G06K 9/6206 |
| | | | 382/294 |
| 2008/0054899 A1* | 3/2008 | Aksoy | G01R 33/5611 |
| | | | 324/307 |
| 2009/0274350 A1* | 11/2009 | Pavlovskaia | G06K 9/32 |
| | | | 382/128 |
| 2010/0046858 A1* | 2/2010 | Yun, II | G06T 7/0028 |
| | | | 382/294 |
| 2010/0249573 A1* | 9/2010 | Marks | G01R 33/4806 |
| | | | 600/411 |
| 2012/0049845 A1* | 3/2012 | Bito | G01R 33/485 |
| | | | 324/309 |
| 2012/0321195 A1 | 12/2012 | Jhunjhunwala et al. | |
| 2013/0187649 A1* | 7/2013 | Bhat | A61B 5/055 |
| | | | 324/307 |
| 2013/0315463 A1* | 11/2013 | Vilsmeier | G01R 33/5608 |
| | | | 382/131 |
| 2015/0154741 A1* | 6/2015 | Chen | G01R 33/543 |
| | | | 348/77 |
| 2015/0324989 A1* | 11/2015 | Smith | G06T 7/00 |
| | | | 382/278 |

OTHER PUBLICATIONS

Wu et al., "Comparison of EPI Distortion Correction Methods in Diffusion Tensor MRI Using a Novel Framework", Med Image Comput Comput Assist Interve, 2008, pp. 321-329.*

Gomez et al., "Accurate High-Resolution Measurements of 3-D Tissue Dynamics With Registration-Enhanced Displacement Encoded MRI", IEEE Transactions on Medical Imaging, vol. 33 No. 6, Jun. 2014, pp. 1350-1362.*

Chang et al., "A Technique for Accurate Magnetic Resonance Imaging in the Presence of Field Inhomogeneities", IEEE Trans. on Medical Imaging, pp. 319-329, vol. 11, Issue 3, Sep. 1992.

Jezzard al., "Correction for Geometric Distortion in Echo Planar Images from B0 Field Variations", Magnetic Resonance in Medicine, pp. 65-73, vol. 34, Issue 1, Jul. 1995.

Chen et al., "Correction for EPI Distortions Using Multi-Echo Gradient-Echo Imaging", Magnetic Resonance in Medicine, pp. 1206-1213, vol. 41, 1999.

Cusack et al., "An Evaluation of the Use of Magnetic Field Maps to Undistort Echo-Planar Images", NeuroImage, pp. 127-142, vol. 18, 2003.

Rohde et al., "Comprehensive Approach for Correction of Motion and Distortion in Diffusion-Weighted MRI", Magnetic Resonance in Medicine, pp. 103-114, vol. 51, 2004.

Priest et al., "EPI Distortion Correction From a Simultaneously Acquired Distortion Map Using Trail", Journal of Magnetic Resonance Imaging, pp. 597-603, vol. 23, 2006.

Xiang et al., "Correction for Geometric Distortion and N/2 Ghosting in EPI by Phase Labeling for Additional Coordinate Encoding (PLACE)", Magnetic Resonance in Medicine, pp. 731-741, vol. 57, 2007.

Liu et al., "Landmark Optimization Using Local Curvature for Point-Based Nonlinear Rodent Brain Image Registration", International Journal of Biomedical Imaging, vol. 2012, Article ID 635207, 8 Pages

* cited by examiner

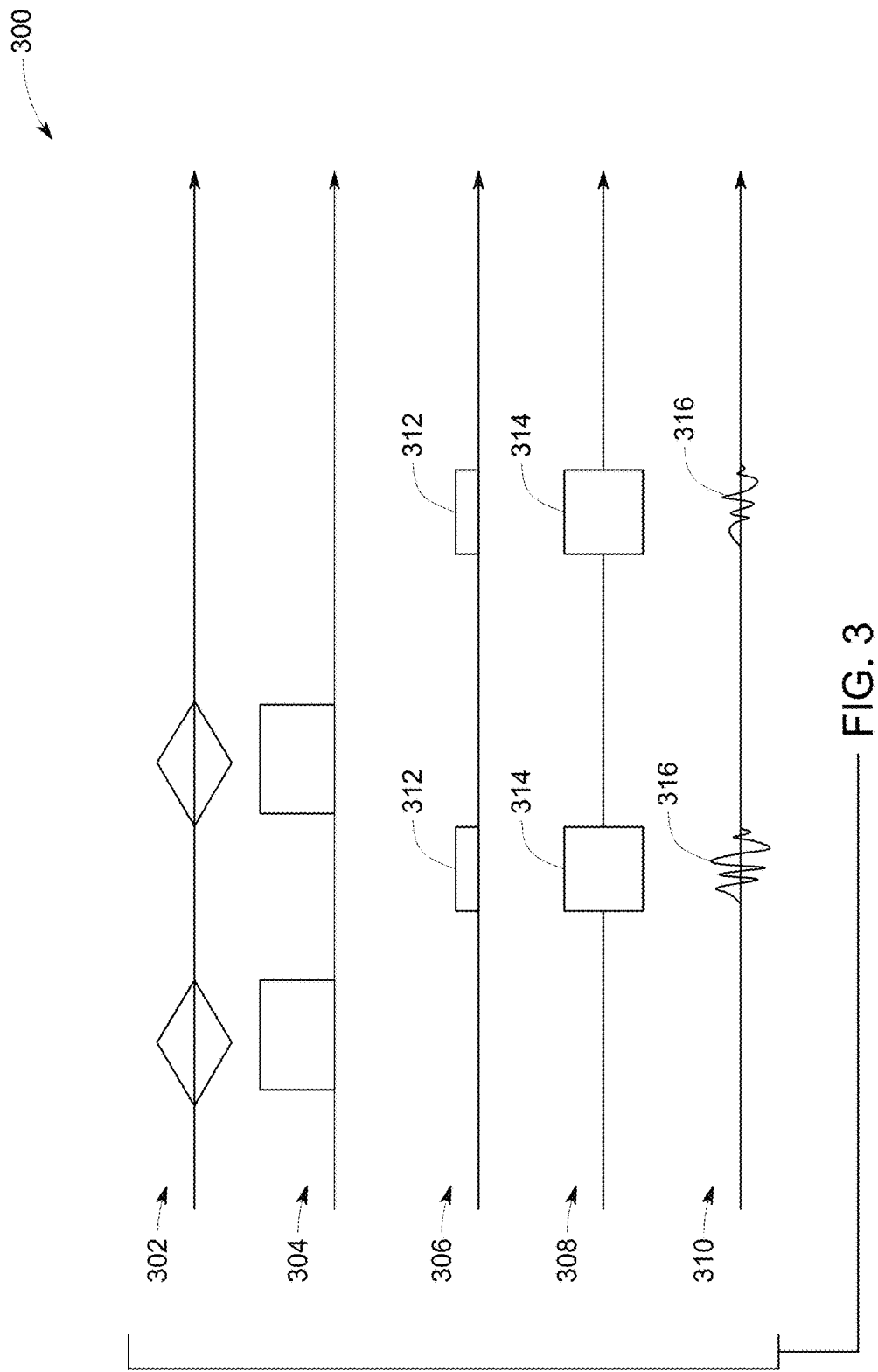

SYSTEM AND METHOD FOR MEDICAL IMAGE CORRECTION

BACKGROUND

A system and method are disclosed for correcting distortion in medical images. Specifically, the subject matter relates to correction of distortion in magnetic resonance images (MRI) due to magnetic field variation.

Echo-planar imaging (EPI) is a fast magnetic resonance (MR) imaging technique that allows acquisition of single images in as little as 20 msec and of an entire image volume in as little as 0.5 seconds. Echo-planar imaging achieves its speed by obtaining all in-plane spatial-encoding information after a single radio-frequency (RF) excitation. EPI can be less sensitive to motion than conventional MR imaging and it allows imaging of rapidly changing physiologic processes such as blood flow and kinetic activity. EPI can be used to shorten scan time, providing new areas of MR imaging research and clinical applications. However, EPI is highly susceptible to image distortion, which results from especially to noises generated due to magnetic field variations and generates distorted images. Spatially varying local and main field inhomogeneity results in geometric distortions in the EPI image. Image voxels may be distorted through compression or stretching, depending on the local field gradients.

Some of the existing techniques measure distortion accurately, and other techniques acquire each data set twice in opposite directions to deduce the translation and intensity correction. Field mapping techniques, commonly used for distortion correction, acquires phase images and measures variations in the magnetic field to calculate local distortion correction pixel shifts in the image. These techniques require longer acquisition times, are susceptible to noise in the data and sometimes suffer from resolution limitations, especially at high fields.

Therefore, better techniques for correcting distortion of MRI image due to magnetic field variation are required.

BRIEF DESCRIPTION

In accordance with one aspect of the present technique, a method is disclosed. The method includes receiving a target image and a reference image. The target image is a distorted magnetic resonance image and the reference image is an undistorted magnetic resonance image. The method further includes selecting an image registration method for registering the target image to the reference image, wherein the image registration method uses an image transformation. The method further includes performing image registration of the target image with the reference image, wherein the image registration provides a plurality of optimized parameters of the image transformation. The method also includes generating a corrected image based on the target image and the plurality of optimized parameters of the image transformation.

In accordance with one aspect of the present technique, a system is disclosed. The system includes at least one processor and a memory communicatively coupled to a communications bus. The system also includes an image acquisition module for receiving a target image and a reference image. The target image is a distorted magnetic resonance image and the reference image is an undistorted magnetic resonance image. The system further includes an image registration module communicatively coupled to the image acquisition module and configured to select an image registration method for registering the target image to the reference image, wherein the registration method uses an image transformation. The image registration module is also configured to perform image registration of the target image with the reference image, wherein the image registration provides a plurality of optimized parameters of the image transformation. The system further includes an image correction module communicatively coupled to the image registration module and configured to generate a corrected image based on the target image and the plurality of optimized parameters of the image transformation. The image acquisition module, the image registration module, and the image correction module are coupled to the communications bus and at least one of them is stored in the memory and executable by the at least one processor.

In accordance with another aspect of the present technique, a non-transitory computer medium encoded with a program is disclosed. The program enables at least one processor to receive a target image and a reference image. The target image is a distorted magnetic resonance image and the reference image is an undistorted magnetic resonance image. The program further enables the at least one processor to select an image registration method for registering the target image to the reference image, wherein the image registration method uses an image transformation. The program further enables the at least one processor to perform image registration of the target image with the reference image, wherein the image registration provides a plurality of optimized parameters of the image transformation. The program also enables the at least one processor to generate a corrected image based on the target image and the plurality of optimized parameters of the image transformation.

DRAWINGS

These and other features and aspects of embodiments of the present invention will become better understood when the following detailed description is read with reference to the accompanying drawings in which like characters represent like parts throughout the drawings, wherein:

FIG. 3 is a diagram illustrating pulse sequence of echo planar imaging (EPI) in according to an exemplary embodiment;

DETAILED DESCRIPTION

Embodiments of methods and systems for correcting distortion in magnetic resonance images (MRI) include receiving a target image, and a reference image. The target image is a distorted magnetic resonance image and the reference image is an undistorted magnetic resonance image corresponding to the target image. An image registration method is selected for registering the target image to the reference image. The image registration method employs an image transformation technique and provides a plurality of optimized parameters of the image transformation. A corrected image is generated based on the target image and the plurality of the optimized parameters of the image transformation.

The term 'image registration' or 'registration' used herein refers to establishing correspondence between features of two images representing same object, feature or an anatomical structure. The term 'image transformation' refers to a mapping of features of one image to the features of another image involved in the image registration process. The term 'optimized parameters' refers to a plurality of numerical values that characterizes the image transformation employed in the image registration. The term metric refers to a function on a pair of images providing a measure of similarity or dissimilarity between the pair of images.

Figure 1:
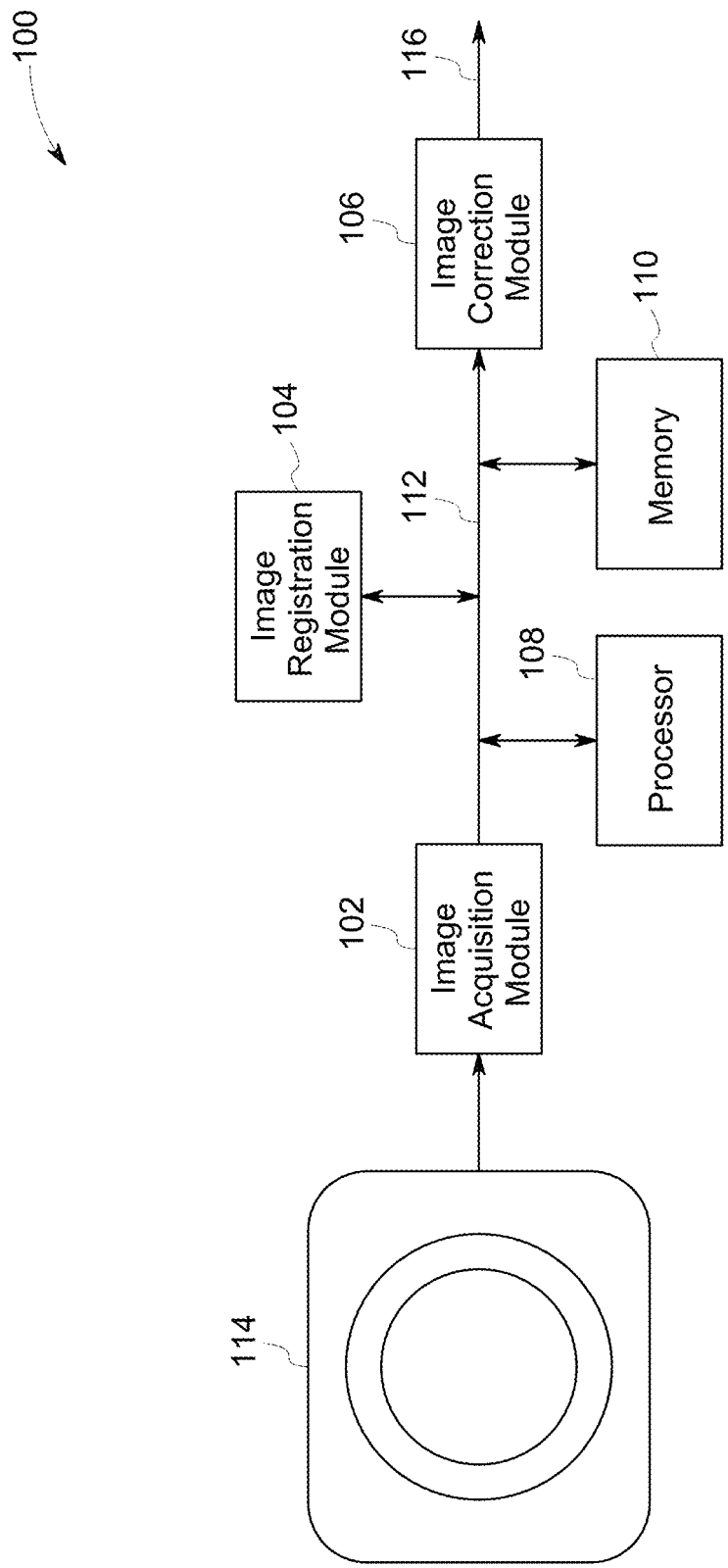
FIG. 1 is a diagrammatic illustration of a system for correcting distortion in MRI image in accordance with an exemplary embodiment.

FIG. 1 is a system 100 for correcting distortion in a magnetic resonance image in accordance with an exemplary embodiment. The system 100 includes an image acquisition module 102, an image registration module 104, and an image correction module 106. The system in some embodiments includes at least one processor 108, and a memory 110 communicatively coupled to other modules via a communications bus 112. Embodiments of the system 100 include an imaging modality 114 generating target images.

The image acquisition module 102 is communicatively coupled to the imaging modality 114 and is configured to receive a target image from the imaging modality 114. The imaging modality in one embodiment is an MRI imaging modality. Specifically, the target image is acquired by employing a fast sampling technique such as echo planar imaging. Application of a slice gradient, a phase encoding gradient pulse, and a frequency encoding gradient pulse to three mutually perpendicular gradient coils of the imaging modality 114 generates an echo response localized in all the three dimensions of the subject. In alternate embodiments, the image acquisition is performed by employing spiral imaging technique. In these embodiments, a homogenous static magnetic field is required around iso-center of the magnet. Differing magnetic properties of a plurality of substances in the subject, generates variations in the magnetic field. The magnetic field variations decreases frequency selection efficacy of pulse signals. The target image acquired with an inhomogeneous magnetic field includes geometric distortion. The target image also includes image distortions due to shorter echo period and shorter repetitive periods used in the fast sampling technique. In an exemplary embodiment, the target image is a distorted magnetic resonance image exhibiting nonlinear spatial inaccuracies. The image acquisition module 102 is also configured to receive a reference image either from the memory 110 or from the imaging modality generating images under a different operating condition. The reference image is an undistorted image corresponding to the target image. In one embodiment, the reference image is acquired by a more robust image acquisition technique such as a spin echo imaging or gradient echo imaging.

The image registration module 104 is communicatively coupled to the image acquisition module 102 and is configured to receive the target image and the reference image from the image acquisition module 102. The image registration module is configured to receive an image transformation technique and a similarity metric from the memory 110. The image transformation includes one or more of parameters. The image registration module is also configured to perform image registration based on an image transformation and a similarity metric. An exemplary technique of image registration is performed in an iterative manner. Each iteration of the image registration technique involves transformation of the target image, computation of similarity metric, comparison with a pre-determined threshold and modification of the parameter of the image transformation using an optimization technique. The image registration technique is explained in subsequent paragraphs with reference to accompanying figures.

The image correction module 106 is communicatively coupled to the image registration module and configured to receive the plurality of optimized parameters of the image transformation and the target image. The image correction module 106 is also configured to generate a corrected image 116 by applying the image transformation with the plurality of optimized parameters to the target image. The corrected image is presented to the user via a display (not shown in figure).

The at least one processor 108 includes at least one arithmetic logic unit, a microprocessor, a general purpose controller or a processor array to perform the desired computations or run the computer program. In one embodiment, the functionality of the at least one processor 108 may be limited to acquire the target image and the reference images. In another embodiment, the functionality of the at least one processor 108 may be limited to perform image registration. In another embodiment, the functionality of the at least one processor 108 is limited to generating the corrected image. In some exemplary embodiments, functionality of the at least one processor would include one or more of the functions of the image acquisition module 102, the image registration module 104, and the image correction module 106. While the processor 108 is shown as a separate unit, there can be a processor co-located or integrated in one or more of the modules 102, 104, 106. Alternatively, the processor 108 can be local or remote, such as a central server or cloud based, with the communications bus 112 can be wired, wireless or a combination thereof.

The memory 110 may be a non-transitory storage medium. For example, the memory 110 may be a dynamic random access memory (DRAM) device, a static random access memory (SRAM) device, flash memory or other memory devices. In one embodiment, the memory 110 may include a non-volatile memory or similar permanent storage device, media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices. In one specific embodiment, a non-transitory computer readable medium may be encoded with a program to instruct the at least one processor 108 to generate a corrected image.

Figure 2:
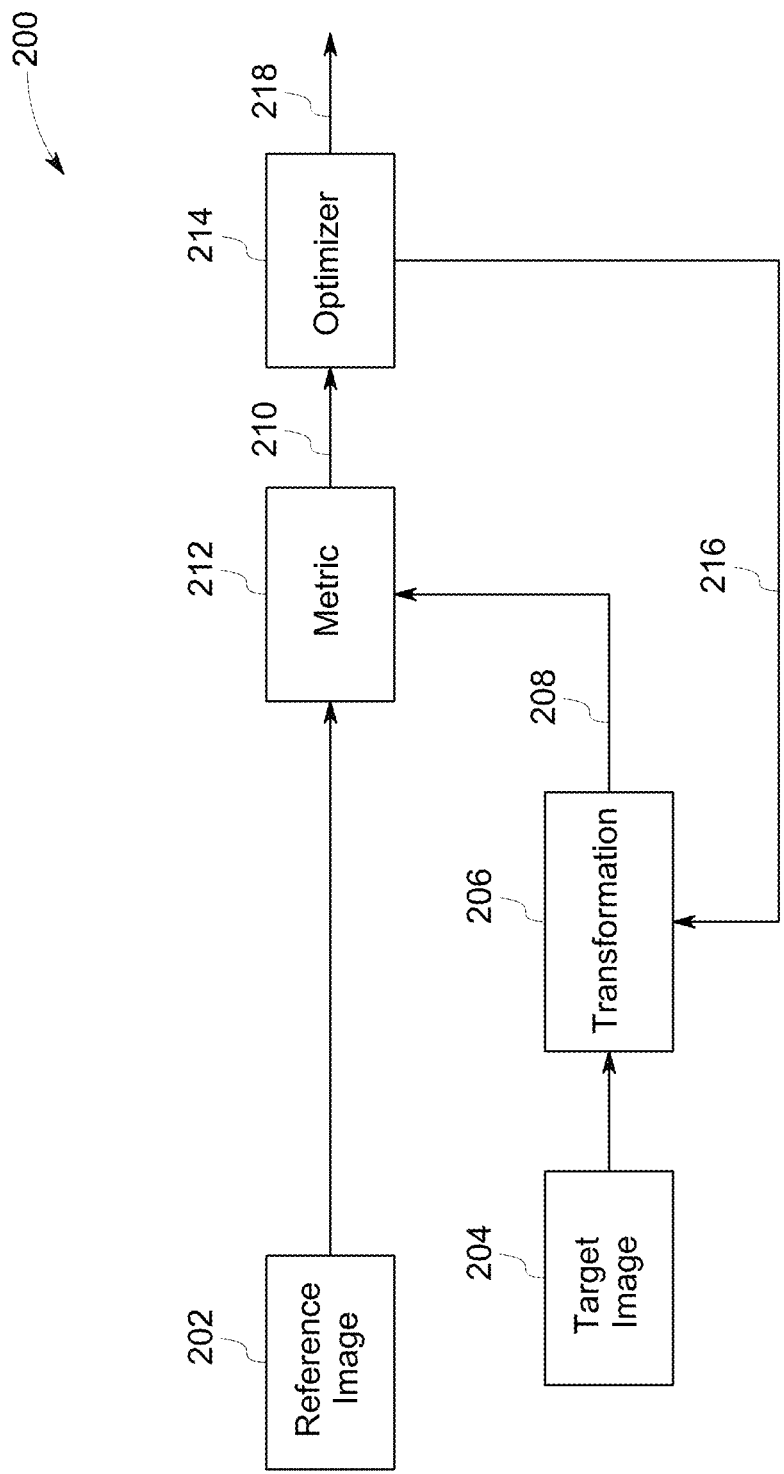
FIG. 2 is a schematic of a system for registration of a targeted image to a reference image in accordance with an exemplary embodiment.

FIG. 2 is a schematic 200 of a system for registration of a targeted image to a reference image in accordance with an exemplary embodiment. The schematic includes a reference image 202, and a target image 204 received by the image acquisition module. The target image 204 is transformed by an image transformation 206 to generate a transformed image 208. In one embodiment, the image transformation used in the registration method is a non-rigid transformation. The non-rigid transformation is based on the fast sampling technique. In an exemplary embodiment, the distortions are introduced in the target image due to phase encoding. The transformation model used in such an embodiment is given by:

$$y = \begin{bmatrix} y_1 \\ y_2 \\ y_3 \end{bmatrix} = \begin{bmatrix} x_1 \\ f_n(x) \\ x_3 \end{bmatrix} \quad (1)$$

where, y is a coordinate in the transformed image, $x=[x_1, x_2, x_3,]^T$ is a coordinate in a target image, $f_n( )$ is a polynomial function of order n. In one exemplary embodiment, when echo planar imaging technique is used, the non-rigid transformation is a polynomial based transformation. In one embodiment, a second order polynomial is used as the polynomial function. The second order polynomial has ten degrees of freedom and is given by:

$$f_2(x)=a_0+a_1x_1+a_2x_2+a_3x_3+a_4x_1x_2+a_5x_1x_3+a_6x_2x_3+a_7x_1^2+a_8x_2^2+a_9x_3^2 \quad (2)$$

where, $a_k$, having k values from zero to nine are constants. In another exemplary embodiment, a third order polynomial is used as the polynomial function. The third order polynomial function has twenty degree of freedom and is given by:

$$f_3(x)=f_2(x)+a_{10}x_1^3+a_{11}x_2^3+a_{12}x_3^3+a_{13}x_1^2x_2+a_{14}x_1^2x_3+a_{15}x_2^2x_1+a_{16}x_2^2x_3+a_{17}x_3^2x_1+a_{18}x_3^2x_2+a_{19}x_1x_2x_3 \quad (3)$$

where, $a_k$, having k values from ten to nineteen are constants. It should be noted herein that the image transformation is a non-linear transformation having reduced computational complexity.

The transformed image 208 and the reference image 202 are compared to determine a similarity measure 210 between the two images 202, 208. The similarity measure 210 is determined using a similarity metric 212 based on the reference image 202 and the transformed image 208. In one embodiment, a normalized mutual information is used as the similarity metric. The normalized mutual information is robust to variations in intensity distributions in the target image and the reference image. The mutual information for two images X and Y is given by $$I(X,Y)=H(X)+H(Y)-H(X,Y)) \quad (4)$$

where, I(X,Y) is the mutual information, H(X) is the entropy of the image X, H(Y) is the entropy of image Y, and H(X,Y) is the joint entropy for the images X, and Y. The entropy for the images X and Y and the joint entropy are given by $$H(X) = \sum_i p_i \log_2(p_i) \quad (5)$$

$$H(Y) = \sum_j p_j \log_2(p_j)$$

$$H(XY) = \sum_i \sum_j p_{ij} \log_2(p_{ij})$$

where, $p_i$, $p_j$, $p_{ij}$ are probabilities of the pixels of the image X, image Y and the joint probability of the ith pixel of the image X and the jth pixel of the image Y. In the exemplary embodiments disclosed herein the image X corresponds to the reference image, the image Y corresponds to the transformed target image. In one embodiment, the mutual information of the transformed target image and the reference image is determined based on the Eq. (4) as the similarity metric. In another embodiment, a normalized mutual information of the transformed target image and the reference given by:

$$I_N(X, Y) = \frac{H(X) + H(Y)}{H(X, Y)} \quad (6)$$

is determined as the similarity metric. In other embodiments, other similarity metric methods such as sum of squared differences between corresponding pixels of the transformed target image and the reference image are determined.

The similarity measure 210 is compared with a pre-determined threshold. The pre-determined threshold is specified by the user or retrieved from a memory location. An optimizer 214 is used to modify the plurality of parameters of the image transformation 206. In an exemplary embodiment, the optimizer 214 is based on a gradient descent optimization technique. In another embodiment, the optimizer 214 is based on the multi resolution optimization technique. When the similarity measure 210 is greater than the pre-determined threshold, the optimizer 214 modifies the plurality of parameters of the image transformation 206 to generate a plurality of modified parameters 216. When the similarity measure 210 is lesser than or equal to the pre-determined threshold, the plurality of modified parameters are considered as a plurality of optimized parameters 218 of the image transformation.

In one exemplary embodiment, the optimizer 214 determines gradient of mutual information $\partial I/\partial A_i$ with reference to the transformation parameter $A_i$. The gradient of the mutual information is used in an optimization technique such as steepest descent method, conjugate gradient method, quasi-Newton method and multiresolution methods. The multiresolution methods may use any of the other optimization technique at each resolutions. The image is sub-sampled and the optimization is performed at a lower resolution using a fraction of the image elements. After convergence, the optimization proceeds to the higher resolution, and eventually covering the full resolution. An objective function used by the optimizer is given by:

$$A_* = \arg \max I(X, T(Y)) \quad (7)$$

where, $A_*$ is the optimized transformation parameters, and the I(X,Y) is the mutual information, T is the transformation model, X is the reference image and Y is the target image.

FIG. 3 is a diagram 300 illustrating pulse sequence of echo planar imaging (EPI) in according to an exemplary embodiment. The pulse sequence is applied to a subject positioned in a static magnetic field with the nuclei spins aligned either along or opposite to the static magnetic field. The pulse sequence includes an RF pulse 302 transmitted to the subject imparting energy to nuclei shifting them to high energy spin state aligned against the magnetic field. In one embodiment, the RF pulse 302 tilts the magnetic field by ninety degrees. In another embodiment, an added second RF pulse provides a refocussing of the magnetic field by further tilting by one hundred and eighty degrees. Such embodiments generate a response signal 310 referred herein as a 'spin echo EPI'. In an alternate embodiment, the first RF pulse tilts the magnetic field by an angle less than ninety degrees. In this embodiment, the response signal 310 is referred as 'gradient echo EPI'. A slice gradient pulse 304 is applied to a suitable gradient coil to select one or a combination of the axial, coronal and sagittal slices of the subject. The slice gradient pulse 304 applied simultaneously with the RF pulse 302 that excite the selected slice in the subject. The thickness of the slice is determined by a slope of the slice gradient pulse 304.

Typically, a phase encoding gradient pulse 306 is applied after the application of the RF pulse 302. The phase encoding gradient pulse localizes the response to a portion of y-axis in the xy plane of the slice. Typically, a frequency encoding gradient pulse 308 is applied after the phase encoding gradient pulse 306. In embodiments involving EPI, the phase encoding gradient pulse 306 is applied along y-axis and the frequency encoding gradient pulse 308 is applied along the x-axis in an interleaved fashion with the phased encoding gradient pulse 306 and the frequency encoding gradient pulse 308 overlapping partially in time. The frequency encoding gradient pulse 308 is also referred herein as 'read out pulse'. The response signal 310 received by receiver coils disposed near the subject, corresponds to a particular point in the spatial frequencies of the xy-plane of the selected slice. In the case of gradient echo EPI, the phase encoding gradient pulse 306 is applied after the first set of RF pulse 302. In the case of spin echo EPI, the phase encoding gradient pulse 306 are applied after the second set of RF pulse 302.

In the exemplary embodiment, a plurality of phase encoding gradient pulses 312 and a plurality of frequency encoding gradient pulses 314 are applied after the excitation of the slice by the slice gradient pulse 304 generating a plurality of echo signals 316. The image acquisition time is reduced but the plurality of echo signals 316 generate a distorted image. The distortions in the image result from imperfections in the main magnetic field corrupting the response signal 310. The distortion in the image worsens with the extent of the interleaving of the phase encoding gradient pulse 306 and the frequency encoding gradient pulse 308. In EPI, distortion increases with the number of read out signals applied after the application of the RF pulse 302. It should be noted herein that having multiple read out pulses in EPI serves to reduce the acquisition time of the image.

In EPI, the distortion is due to interleaving by the phase encoding along y-axis. An image transformation characterizing the distortion modifies y-coordinate of pixels of the target image. In an exemplary embodiment, the image transformation is provided by the transformation equation given by Equation. 1. In other exemplary embodiments, other fast imaging techniques employ similar image transformations along at least one of the co-ordinate axes. The exemplary embodiments disclosed herein generate an optimum image transformation for reducing distortions in the acquired target image.

Figure 4:
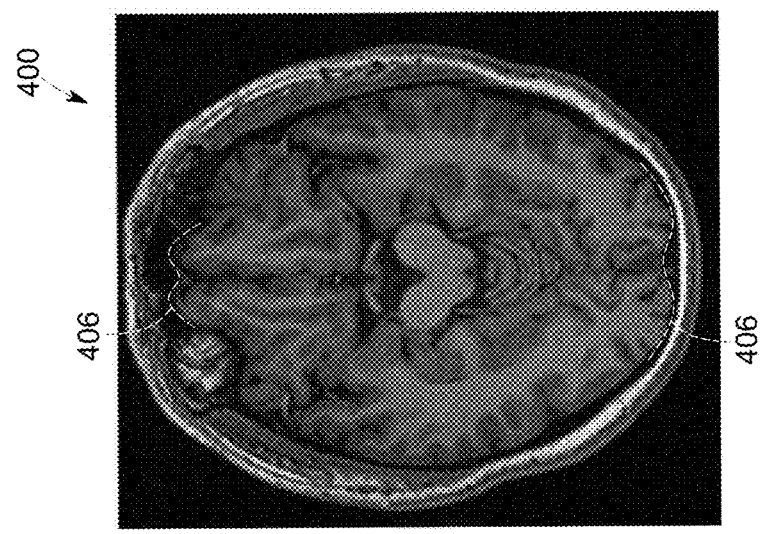
FIG. 4 illustrates a reference image used in the image correction technique in accordance with an exemplary embodiment.

FIG. 4 illustrates a reference image 400 used in the image correction technique in accordance with an exemplary embodiment. The reference image 400 is a brain image acquired with MRI using a conventional method such as a gradient echo method or a spin echo method. The reference image 400 includes anterior and posterior boundaries, illustrated by dashed lines 406. The reference image 400 is free from spatial distortion and the perceived boundaries of brain are aligned with the dashed lines 406.

Figure 5:
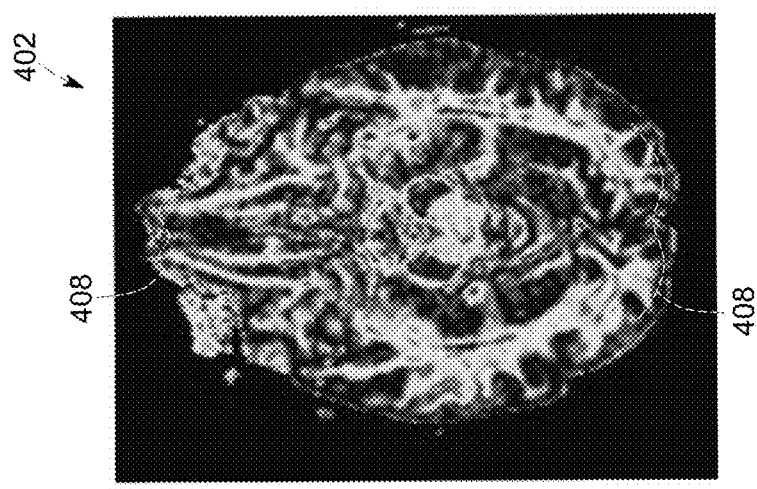
FIG. 5 illustrates a target image acquired by a fast imaging technique used in the image correction technique in accordance with an exemplary embodiment.

FIG. 5 illustrates a target image 402 acquired by a fast imaging technique used in the image correction technique in accordance with an exemplary embodiment. The target image 402 is an MRI image of brain acquired from a fast imaging method such as EPI. The target image generated by the fast imaging technique includes image distortions. The target image 402 is registered via rigid registration to the reference image 400. The dashed lines 406 of the undistorted reference image 400 are transferred to the registered target image 402 and are illustrated by dashed lines 408. It should be noted that the dashed lines 408 do not match with the perceived image boundaries of the target image 402. The extent of mismatch is indicative of magnitude of spatial misalignment distortion in the target image 402.

Figure 6:
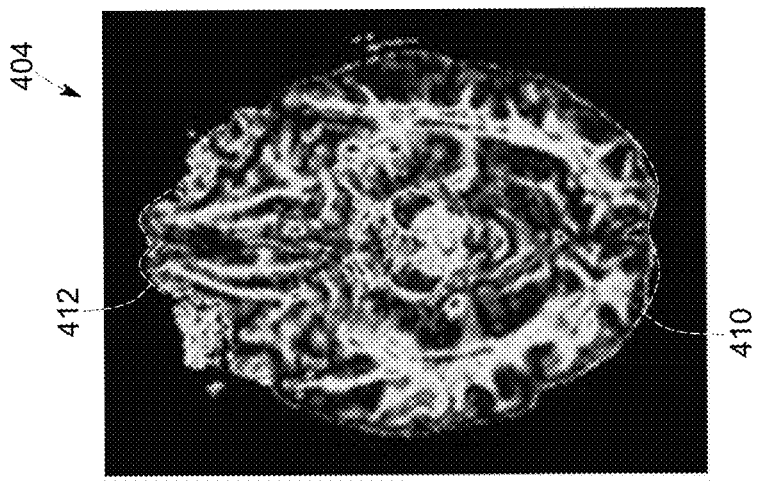
FIG. 6 illustrates a corrected image generated by applying the disclosed technique on the target image in a accordance with an exemplary embodiment.

FIG. 6 illustrates a corrected image 404 generated by applying the disclosed technique on the target image 402 in accordance with an exemplary embodiment. The corrected image 404 is an MRI image of the brain processed by the disclosed technique to determine a distortion free image. The boundary lines transferred from the reference image 400 are represented by the dashed lines 410, 412. It should be noted herein that the boundary lines 410, 412 of the corrected image 404 match closely with the perceived image boundaries from the corrected image 404.

Figure 7:
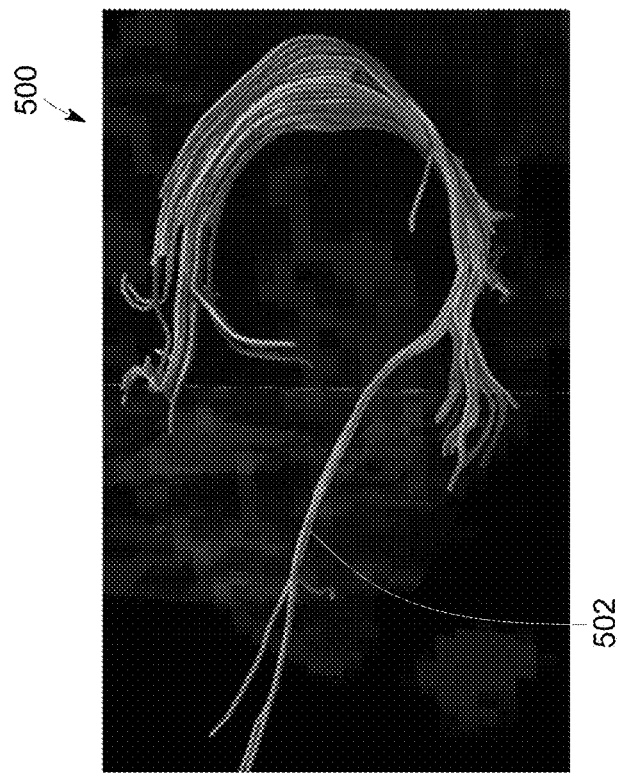
FIG. 7 illustrates a tractographic image of the target image having distortions in accordance with an exemplary embodiment.

FIG. 7 illustrates a tractographic target image 500 of a human brain having distortions in accordance with an exemplary embodiment. Tractographic representation is based on diffusion imaging acquired with the EPI technique. The target image 500 is representative of the arcuate fasciculus of the human brain. The arcuate fasciculus, meaning 'curved bundle', is a bundle of axons that forms part of a pair of long bi-directional bundles of neurons connecting the front and the back of the cerebrum (superior longitudinal fasciculus). The arcuate bi-directionally connects the caudal temporal cortex to the inferior parietal cortex to locations in the frontal lobe. The target image 500 exhibits integration of a plurality streamlines in the form of fiber like structures in different colors. The distortion in the image is illustrated in a misdirected streamline 502 representing false connections between regions of the brain.

Figure 8:
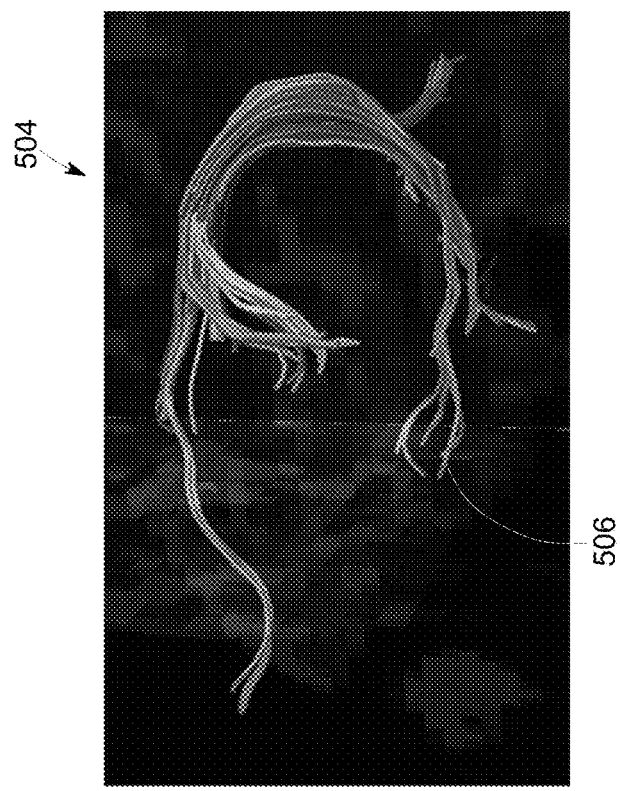
FIG. 8 illustrates a tractographic image of a corrected image in accordance with an exemplary embodiment.

FIG. 8 illustrates a tractographic corrected image 504 of the human brain in accordance with an exemplary embodiment. The corrected image 504 exhibits a corrected streamline 506 generated by applying the disclosed technique to the target image represented by the target image 500. The corrected image 504 shows corrected streamline 506 that conform to the expected anatomy, displaying the correct connections due to improved spatial alignment.

Figure 9:
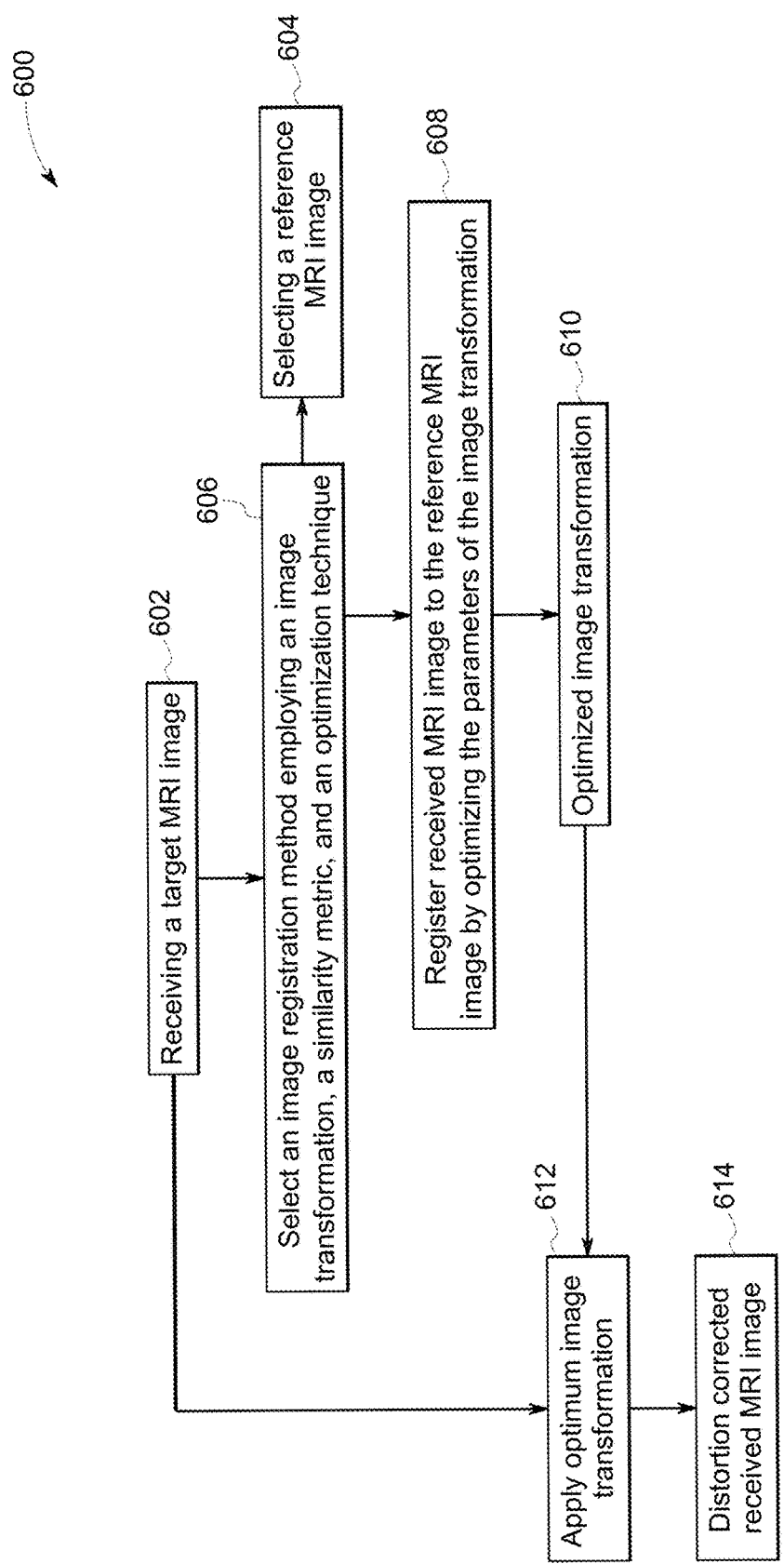
FIG. 9 is a flow chart of a method of correcting distortion in MRI image in accordance with an exemplary embodiment.

FIG. 9 is a flow chart 600 of a method of correcting distortion in MRI image in accordance with an exemplary embodiment. The method includes receiving a target image having distortions, acquired from a fast sampling technique such an echo planar imaging (EPI) 602. A reference image having no distortions, corresponding to the distorted target image is also received 604. An image registration method is selected for registering the target image to the reference image 606. The image registration method employs an image transformation, a similarity metric, and an optimization technique. The image transformation is used to transform the target image to align with the reference image and the similarity metric is used to determine a similarity value between transformed target image and the reference image. The optimization method is used for modifying the parameters of the image transformation. The target image is registered to the reference image by modifying the parameters of the image transformation using the optimization method 608. The plurality of optimized parameters of the image transformation used for registering purposes is determined by the image registration technique 610. The optimum image transformation is used to modify the target image 612 to generate a distortion corrected target image 614.

Embodiments of the disclosed technique generate a corrected image by processing the distorted target image. The processing of the distorted target image includes transforming the target image by an optimum image transformation determined by registering the target image to the reference image. In the case of distortions arising from EPI readout, the image transformation is based on a non-linear polynomial that effectively models nonlinear spatial variations caused by the magnetic field variations. The benefits of using the optimum image transformations of the proposed technique is that the number of transformation parameters can be reduced, thereby reducing the computational complexity, and avoiding local extrema while determining the optimal parameters of the image transformation.

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the specification is not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the specification may include only some of the described embodiments. Accordingly, the specification is not to be seen as limited by the foregoing description, but is only limited by the scope of the appended claims.

The invention claimed is:

1. A method, comprising:
   receiving a target image, wherein the target image is a distorted magnetic resonance image comprising distortions in y-coordinates of pixels of the target image based on application of phase encoding gradient pulse along a y-axis and frequency encoding gradient pulse along an x-axis in an interleaved fashion;
   receiving a reference image, wherein the reference image is an undistorted magnetic resonance image;
   selecting an image registration method for registering the target image to the reference image, wherein the image registration method uses an image transformation to reduce distortions, wherein the image transformation consists of modifying the y-coordinates of the pixels based on corresponding pixels of the reference image using a polynomial function;
   performing image registration of the target image with the reference image, wherein the image registration provides a plurality of optimized parameters of the image transformation; and
   generating a corrected image based on the target image and the plurality of optimized parameters of the image transformation.

2. The method of claim 1, wherein receiving the target image comprises acquiring a magnetic resonance image by a fast sampling technique.

3. The method of claim 1, wherein receiving the target image comprises acquiring a magnetic resonance image by an echo planar imaging technique.

4. The method of claim 1, wherein the distortions in the y-coordinates of the pixels of the target image comprises image distortion due to magnetic field variations.

5. The method of claim 1, wherein performing the image registration comprises transforming the target image based on a non-rigid transformation.

6. The method of claim 5, wherein the non-rigid transformation is based on a third order non-linear polynomial function.

7. The method of claim 1, wherein performing the image registration comprises determining a similarity value based on a similarity metric.

8. The method of claim 7, wherein determining the similarity value comprises computation of a normalized mutual information.

9. The method of claim 1, wherein performing the image registration comprises determining the plurality of optimized parameters of the image transformation based on an optimization technique.

10. The method of claim 9, wherein the optimization technique comprises a gradient based method.

11. A system, comprising:
    at least one processor and a memory communicatively coupled to a communications bus;
    an image acquisition module for receiving a target image and a reference image, wherein the target image is a distorted magnetic resonance image and the reference image is an undistorted magnetic resonance image, and wherein the target image comprises distortions in y-coordinates of pixels based on application of phase encoding gradient pulse along a y-axis and frequency encoding gradient pulse along an x-axis in an interleaved fashion;
    an image registration module communicatively coupled to the image acquisition module and configured to:
       select an image registration method for registering the target image to the reference image, wherein the image registration method uses an image transformation to reduce distortions, wherein the image transformation consists of modifying the y-coordinates of the pixels of the target image based on corresponding pixels of the reference image using a polynomial function;
       perform image registration of the target image with the reference image, wherein the image registration provides a plurality of optimized parameters of the image transformation; and
    an image correction module communicatively coupled to the image registration module and configured to generate a corrected image based on the target image and the plurality of optimized parameters of the image transformation,
    wherein the image acquisition module, the image registration module, and the image correction module are coupled to the communications bus, and wherein at least one of the image acquisition module, the image registration module, and the image correction module is stored in the memory and executable by the at least one processor.

12. The system of claim 11, wherein the image acquisition module is configured to acquire the target image using a fast sampling technique.

13. The system of claim 11, wherein the image acquisition module is configured to acquire the target image using an echo planar imaging technique.

14. The system of claim 11, wherein the image acquisition module introduces image distortion due to magnetic field variations.

15. The system of claim 11, wherein the image registration module is configured to perform a non-rigid transformation of the target image.

16. The system of claim 15, wherein the image registration module is configured to transform the target image based on a third order non-linear polynomial function.

17. The system of claim 11, wherein the image registration module is further configured to determine a similarity value based on a similarity metric.

18. The system of claim 17, wherein the image registration module is further configured to determine a normalized mutual information.

19. The system of claim 11, wherein the image registration module is further configured to determine the plurality of optimized parameters of the image transformation based on an optimization technique.

20. The system of claim 19, wherein the image registration module is further configured to perform a gradient based optimization technique.

21. A non-transitory computer readable medium encoded with a program to enable at least one processor to:

receive a target image, wherein the target image is a distorted magnetic resonance image comprising distortions in y-coordinate of pixels of the target image based on application of phase encoding gradient pulse along a y-axis and frequency encoding gradient pulse along x-axis in an interleaved fashion;

receive a reference image, wherein the reference image is an undistorted magnetic resonance image;

select an image registration method for registering the target image to the reference image, wherein the image registration method uses an image transformation to reduce distortions, wherein the image transformation consists of modifying the y-coordinates of the pixels based on corresponding pixels of the reference image using a polynomial function;

perform image registration of the target image with the reference image, wherein the image registration provides a plurality of optimized parameters of the image transformation; and generate a corrected image based on the target image and the plurality of the optimized parameters of the image transformation.

* * * * *